United States Patent [19]
Otani et al.

[11] 4,291,021
[45] Sep. 22, 1981

[54] NOVEL MACROLIDE ANTIBIOTICS AND PREPARATION THEREOF

[75] Inventors: Masaru Otani; Shuzo Satoi; Naoki Muto; Tetsu Saito, all of Shizuoka; Tadashiro Fujii, Mishima; Seiji Katsumata, Susono; Mitsuo Hayashi; Masaru Ono, both of Shizuoka, all of Japan

[73] Assignee: Toyo Jozo Company, Ltd., Shizuoka, Japan

[21] Appl. No.: 37,846

[22] Filed: May 10, 1979

[30] Foreign Application Priority Data

May 10, 1978 [JP] Japan .................................. 53-54373
Mar. 2, 1979 [JP] Japan .................................. 54-24788
Mar. 16, 1979 [JP] Japan .................................. 54-31316

[51] Int. Cl.³ ...................... C12P 19/60; A61K 35/74
[52] U.S. Cl. .................................. 424/121; 424/122; 435/75; 435/76; 435/169; 435/867
[58] Field of Search ................... 435/75, 76, 128, 867, 435/170, 169; 424/121, 122

[56] References Cited

U.S. PATENT DOCUMENTS

4,032,631  6/1977  Celmer et al. .................... 424/121
4,162,305  7/1979  Nara et al. ......................... 435/867

FOREIGN PATENT DOCUMENTS

47-23548  6/1972  Japan .................................. 424/121
50-145588  11/1975  Japan .................................. 435/867

Primary Examiner—Benoît Castel
Attorney, Agent, or Firm—Craig and Antonelli

[57] ABSTRACT

A novel microorganism species belonging to the genus Micromonospora, i.e. Micromonospora sp. A 11725 is found to be capable of producing novel macrolide antibiotics A 11725 I, A 11725 II and A 11725 III. Novel antibiotics A 11725 Ia and A 11725 IIa are also found to be derived by chemical modification of the antibiotics A 11725 I and A 11725 II, respectively. All of these antibiotics or salts thereof exhibit excellent antibacterial and anti-mycoplasmal activities against various microorganisms such as Staphylococcus or Mycoplasma, and therefore useful for various purposes including medicaments.

11 Claims, 15 Drawing Figures

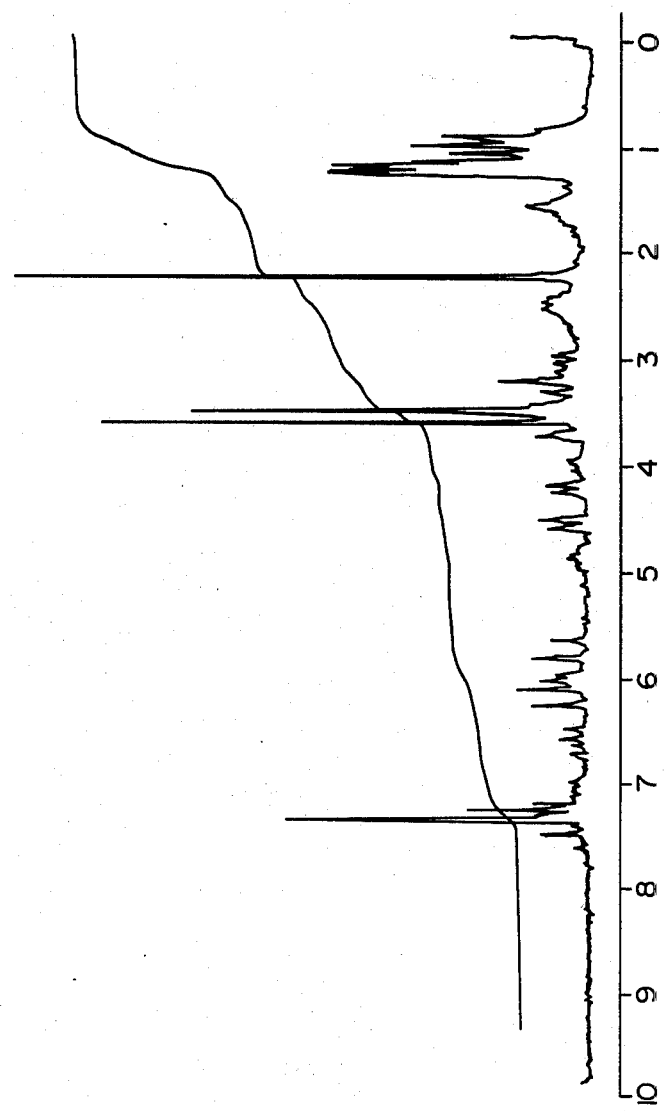
F I G. 12

NOVEL MACROLIDE ANTIBIOTICS AND PREPARATION THEREOF

This invention relates to novel macrolide antibiotic substances exhibiting excellent anti-bacterial and anti-mycoplasmal activities against microorganisms such as Staphylococcus or Mycoplasma, processes for producing the same and the microorganism for producing said substances.

Figure 1:
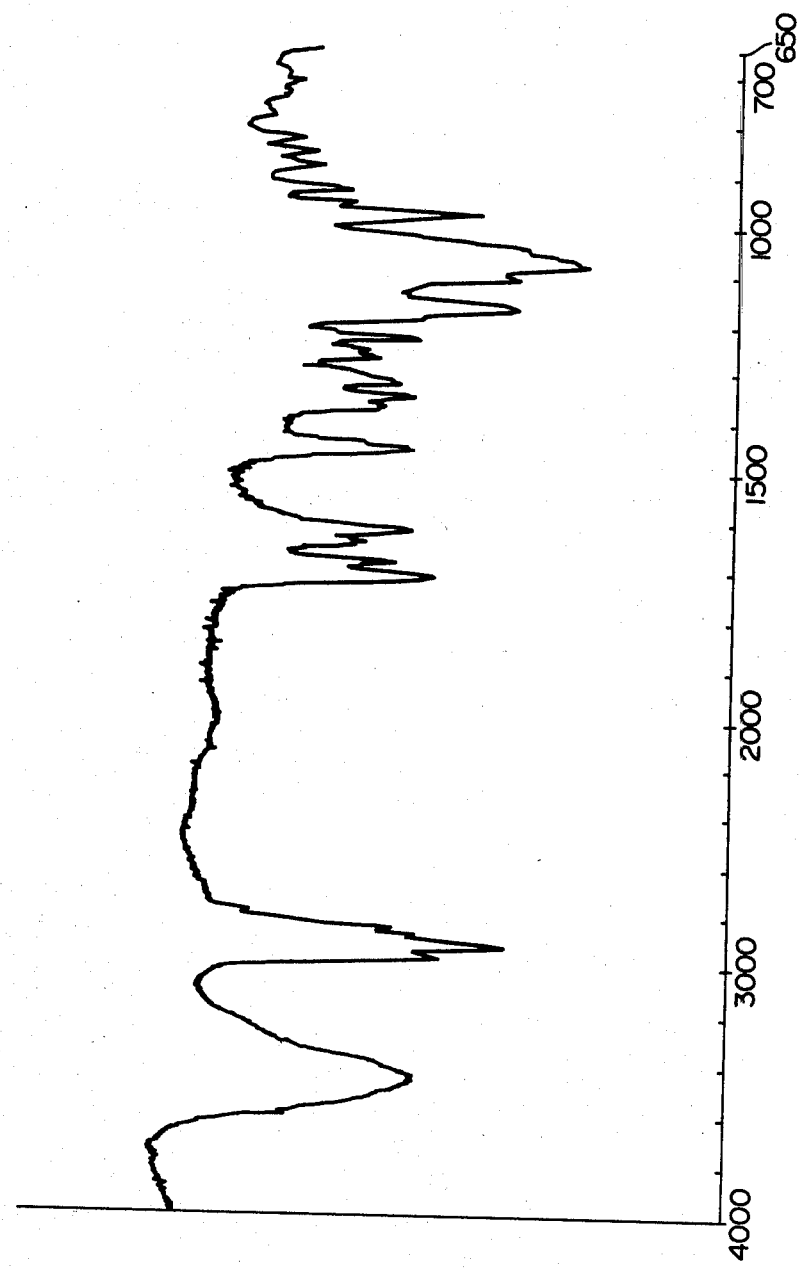
Figure 2:
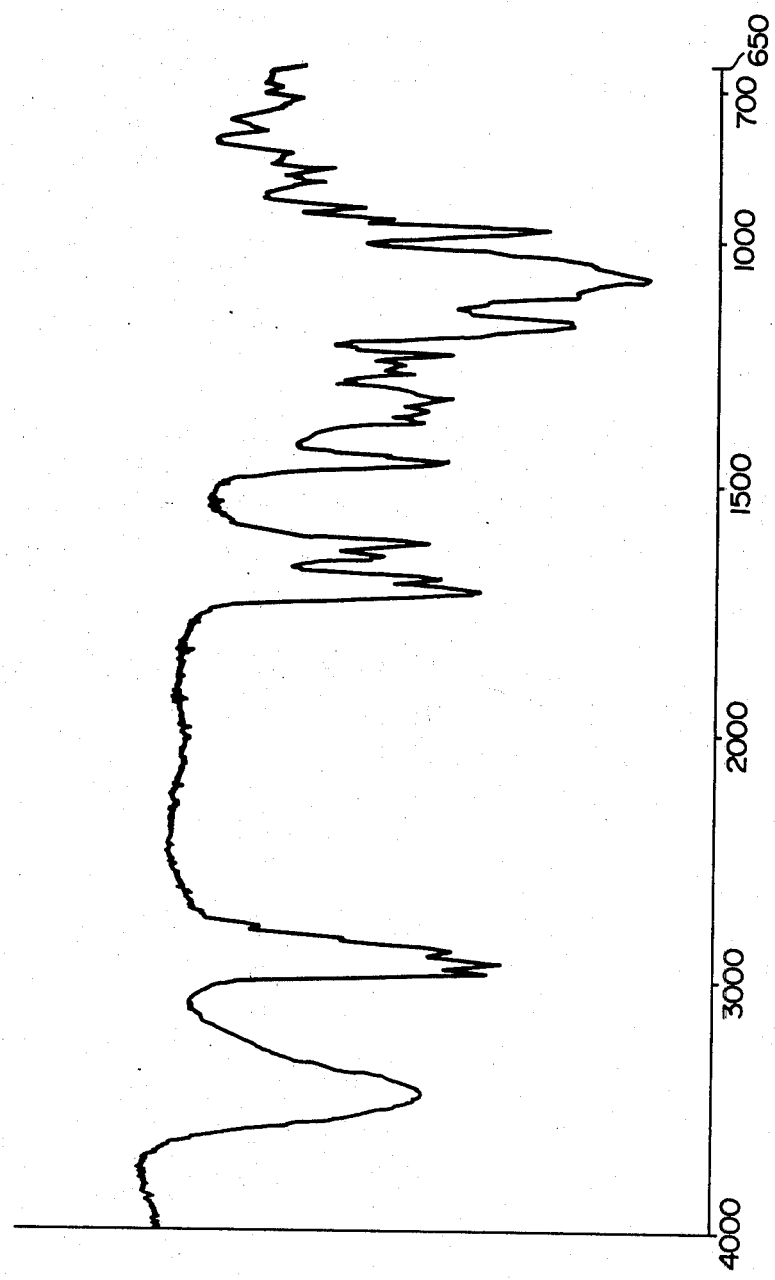
Figure 3:
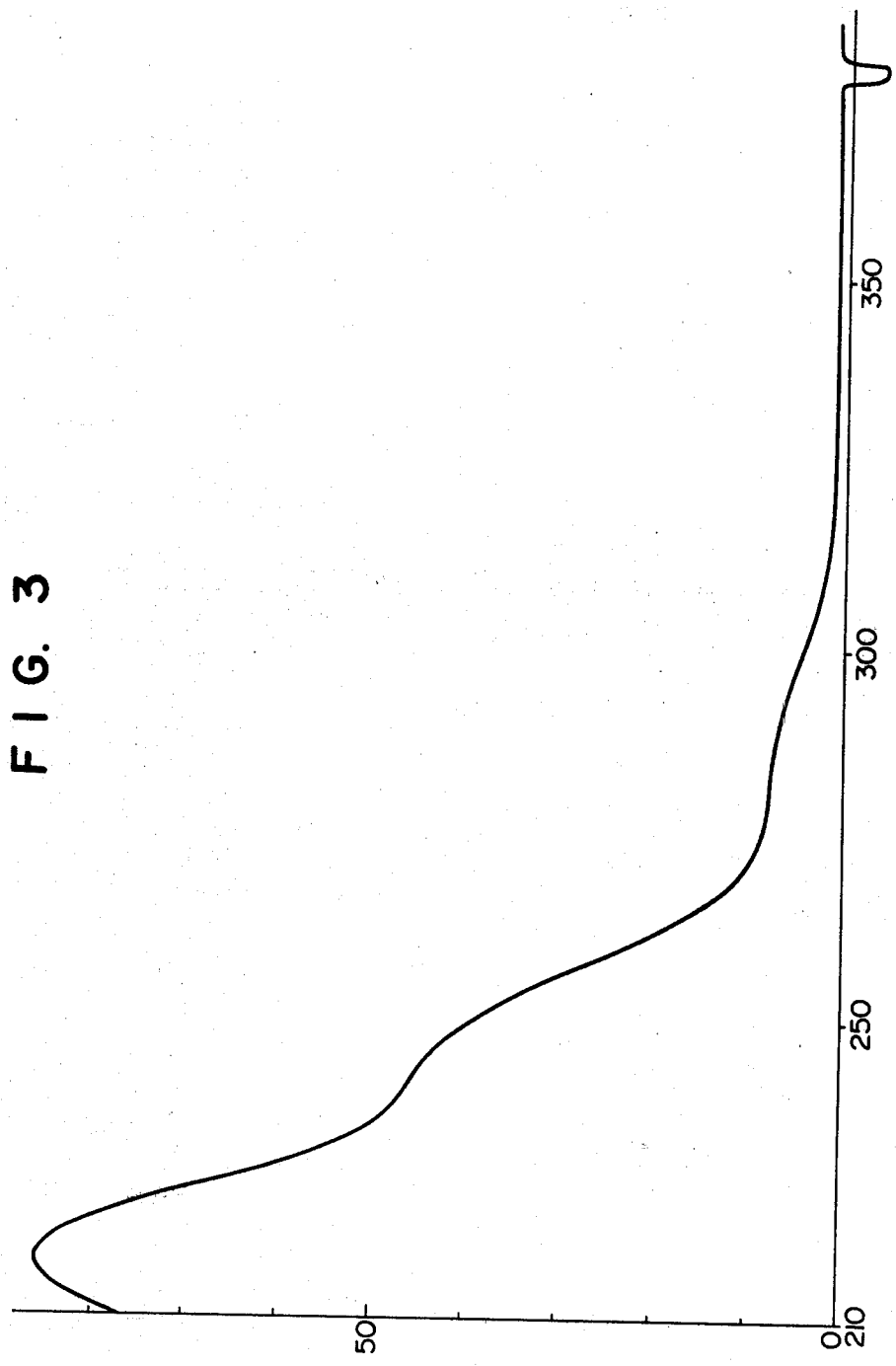
Figure 4:
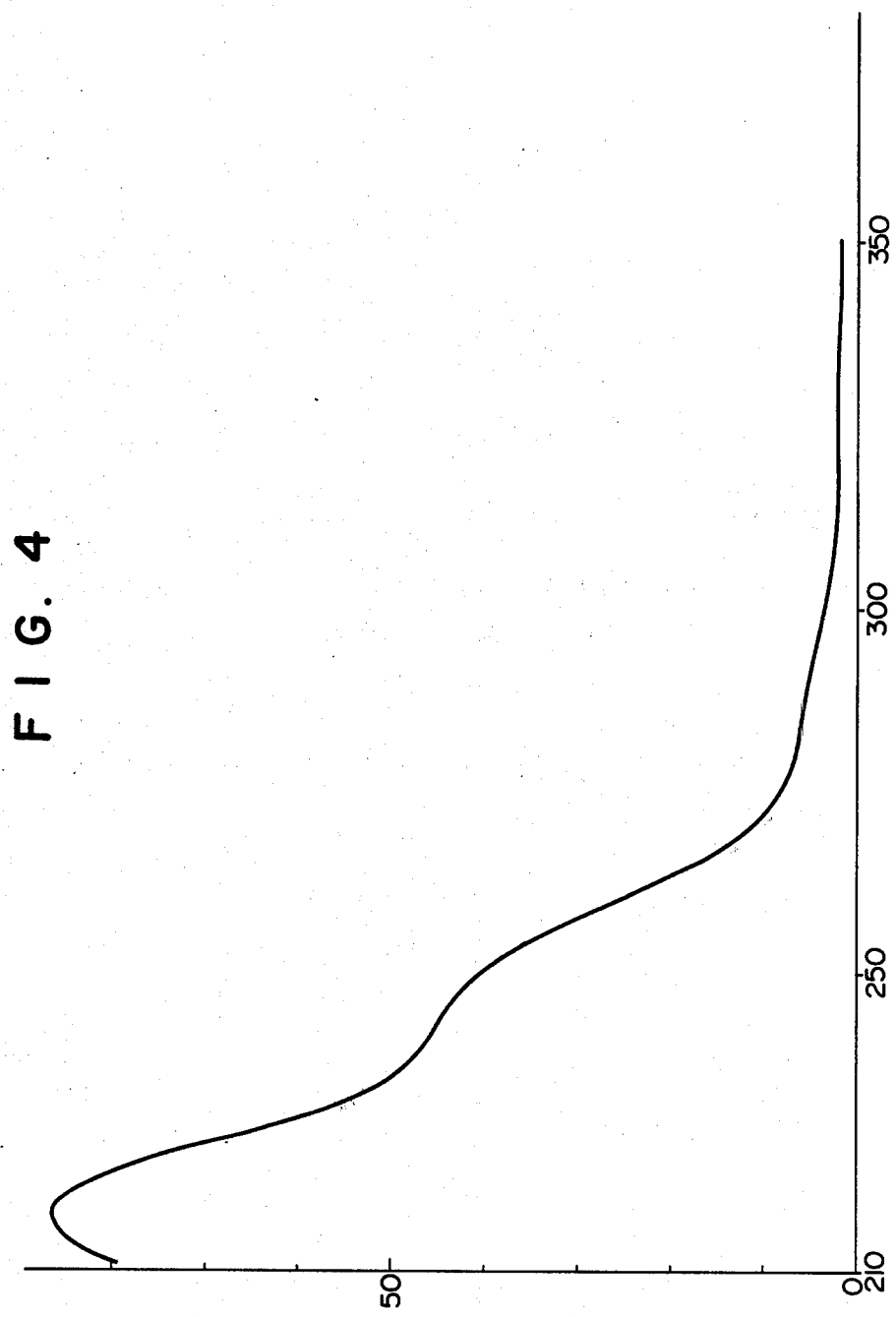
Figure 5:
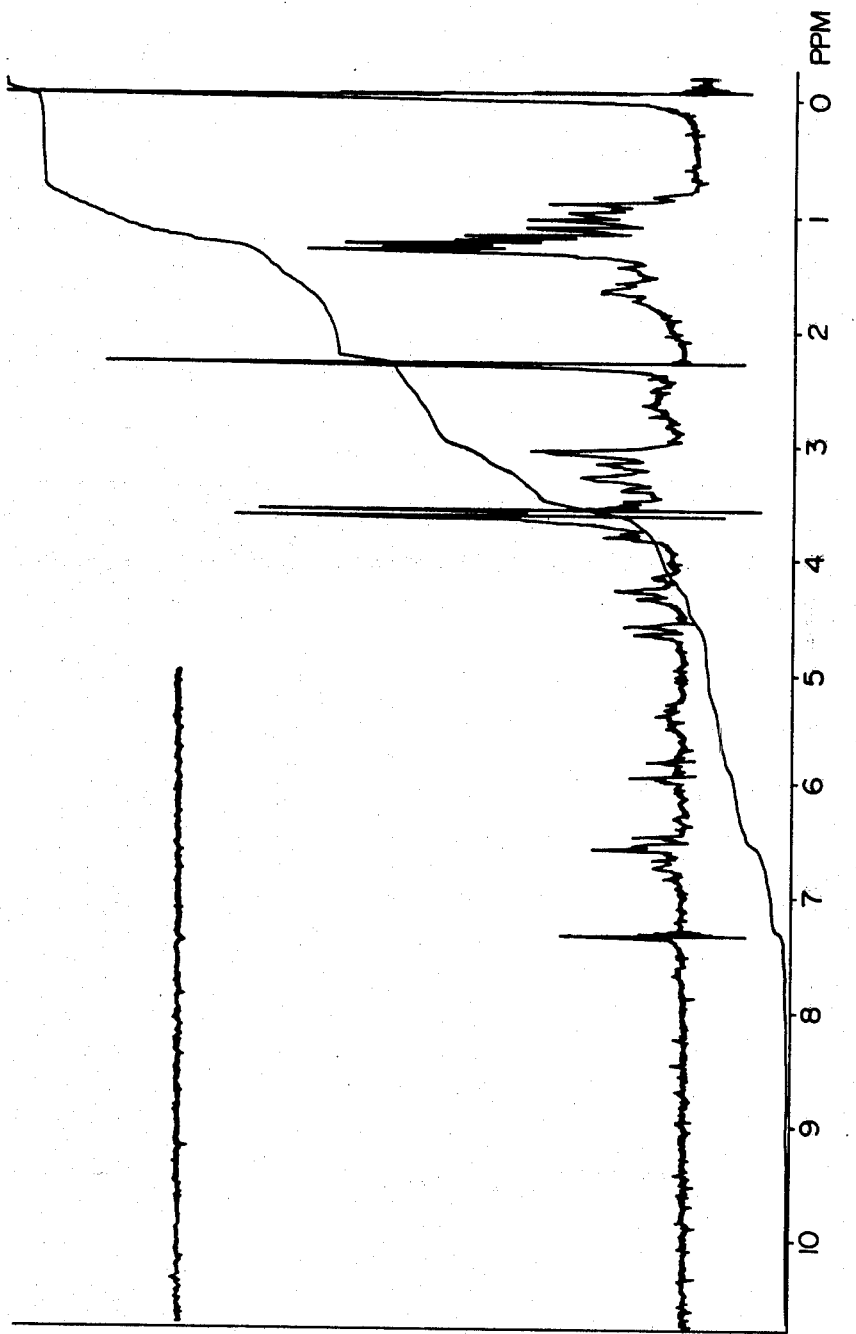
Figure 6:
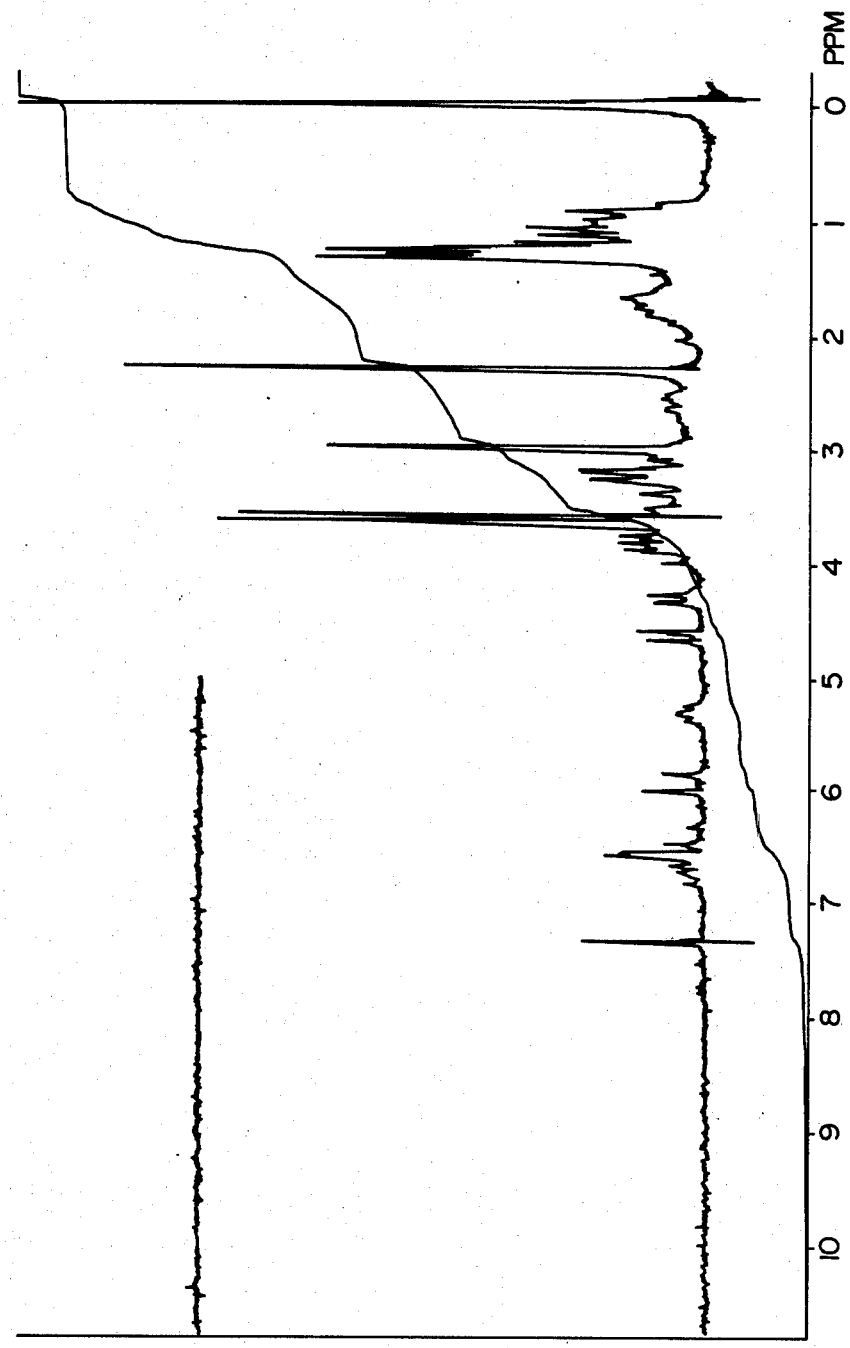
Figure 7:
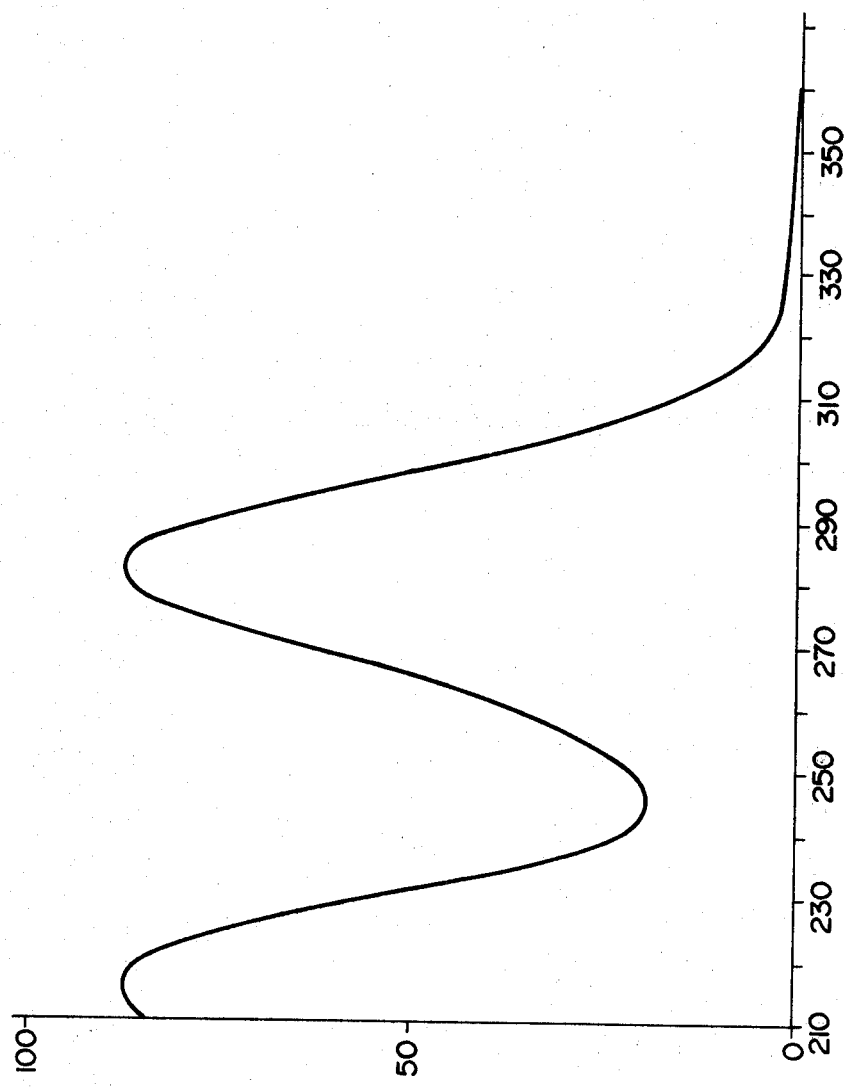
Figure 8:
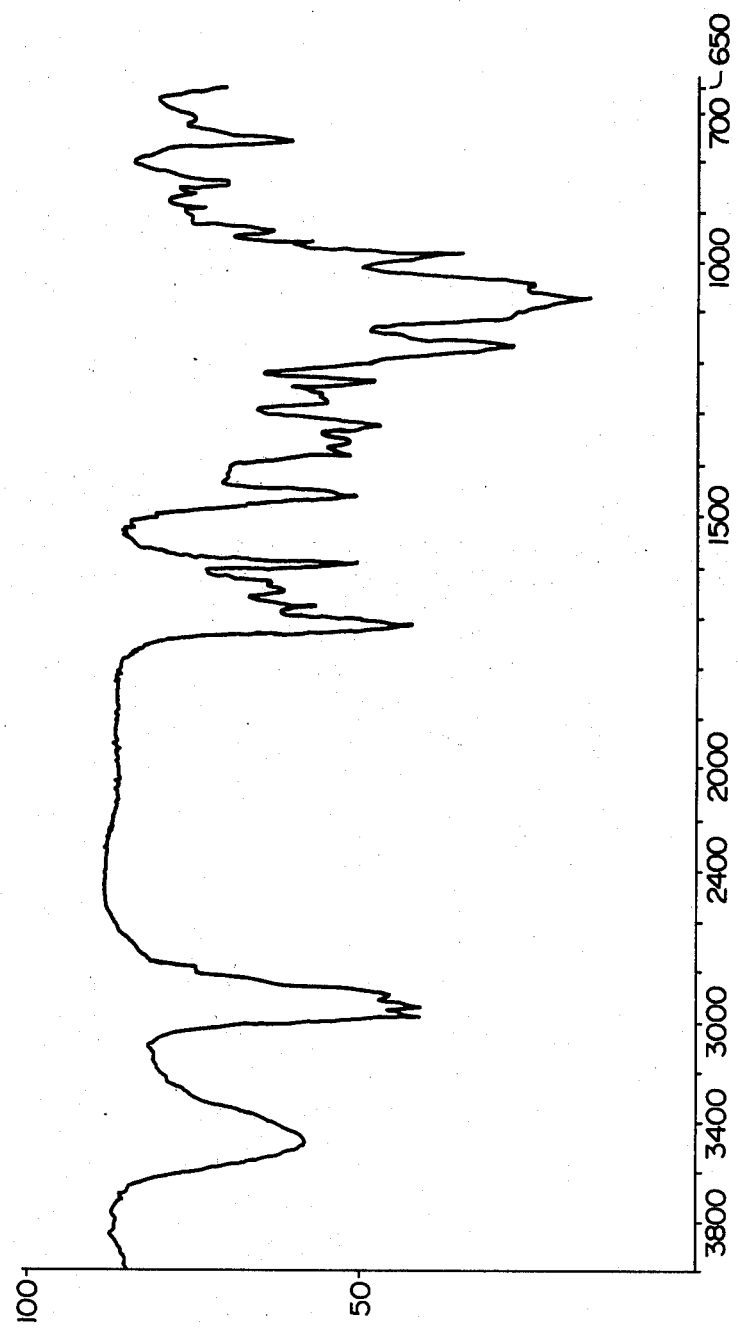
Figure 9:
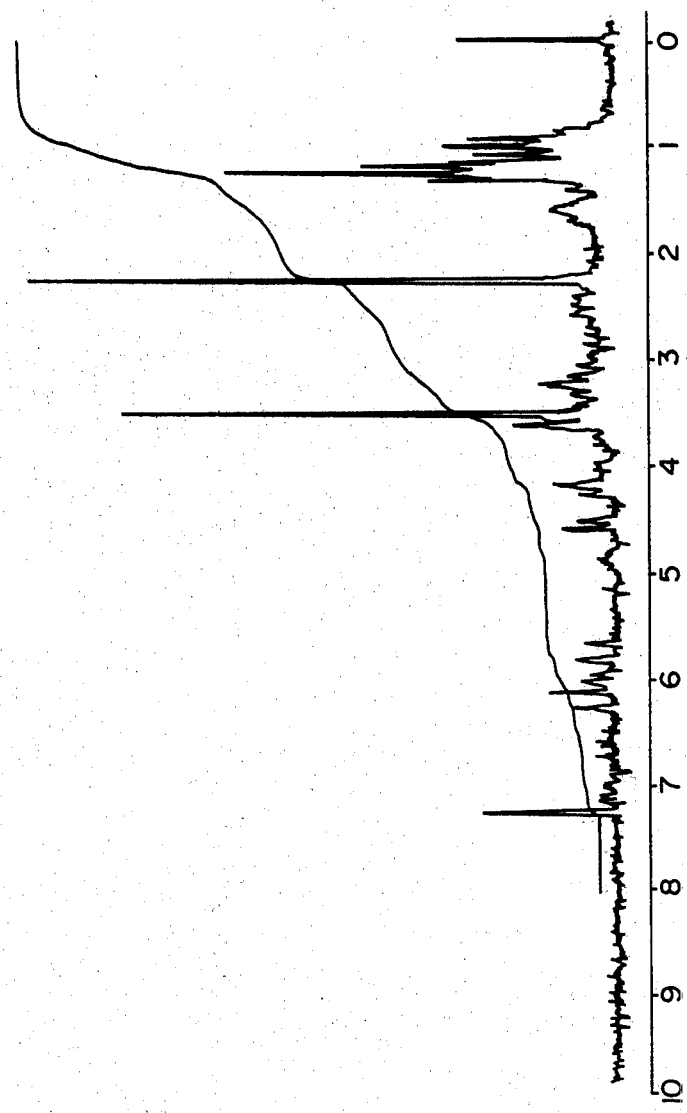
Figure 10:
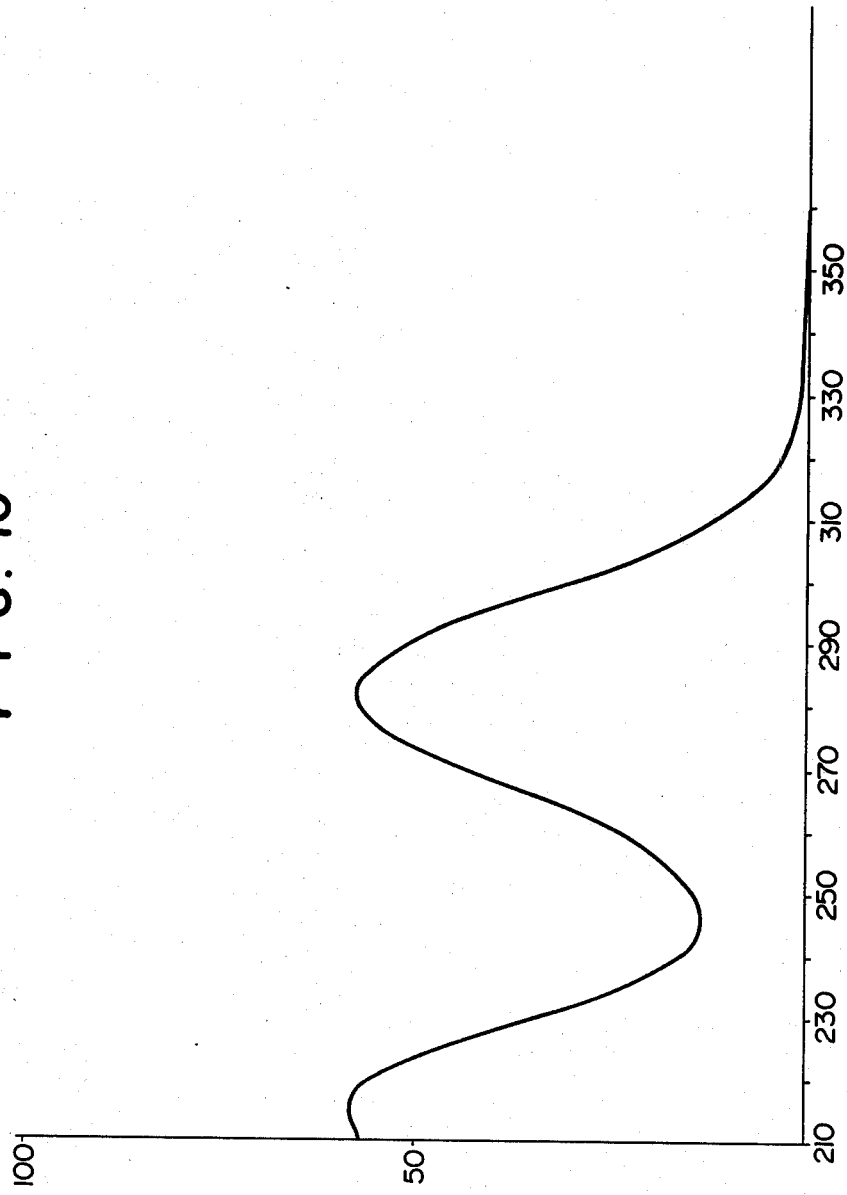
Figure 11:
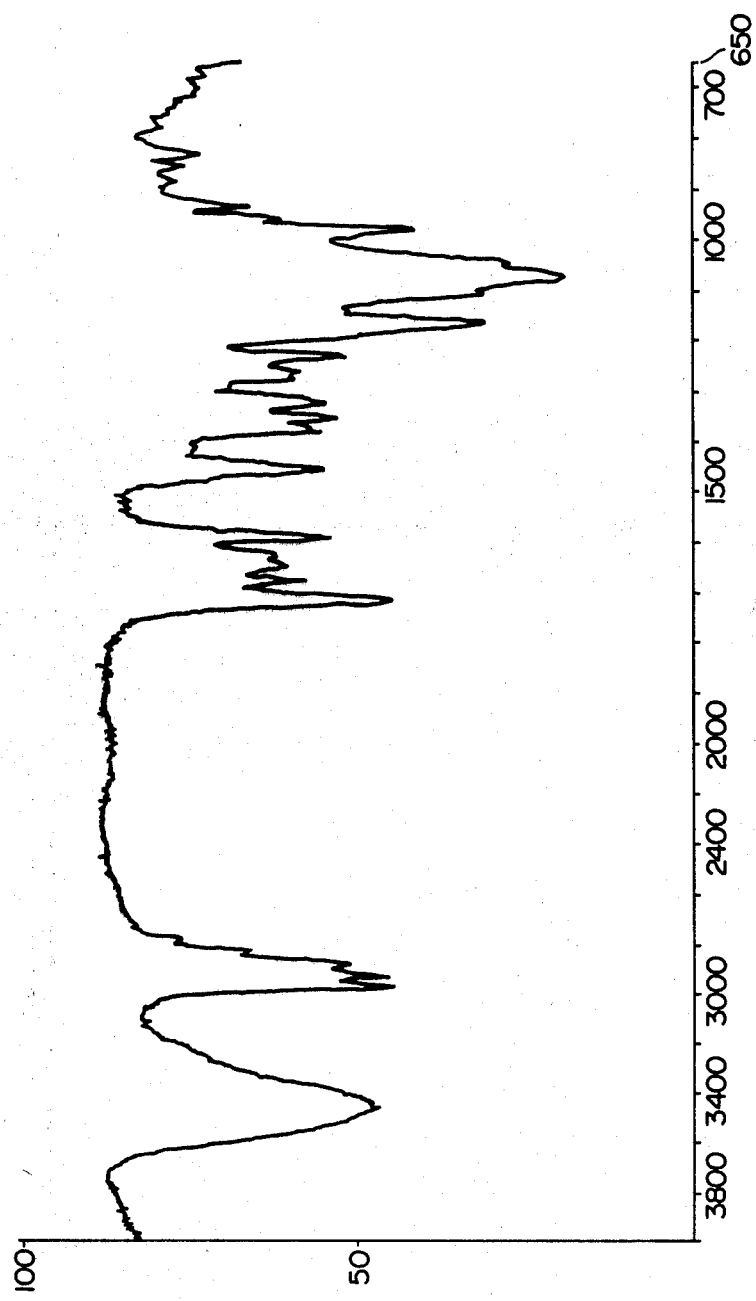
Figure 13:
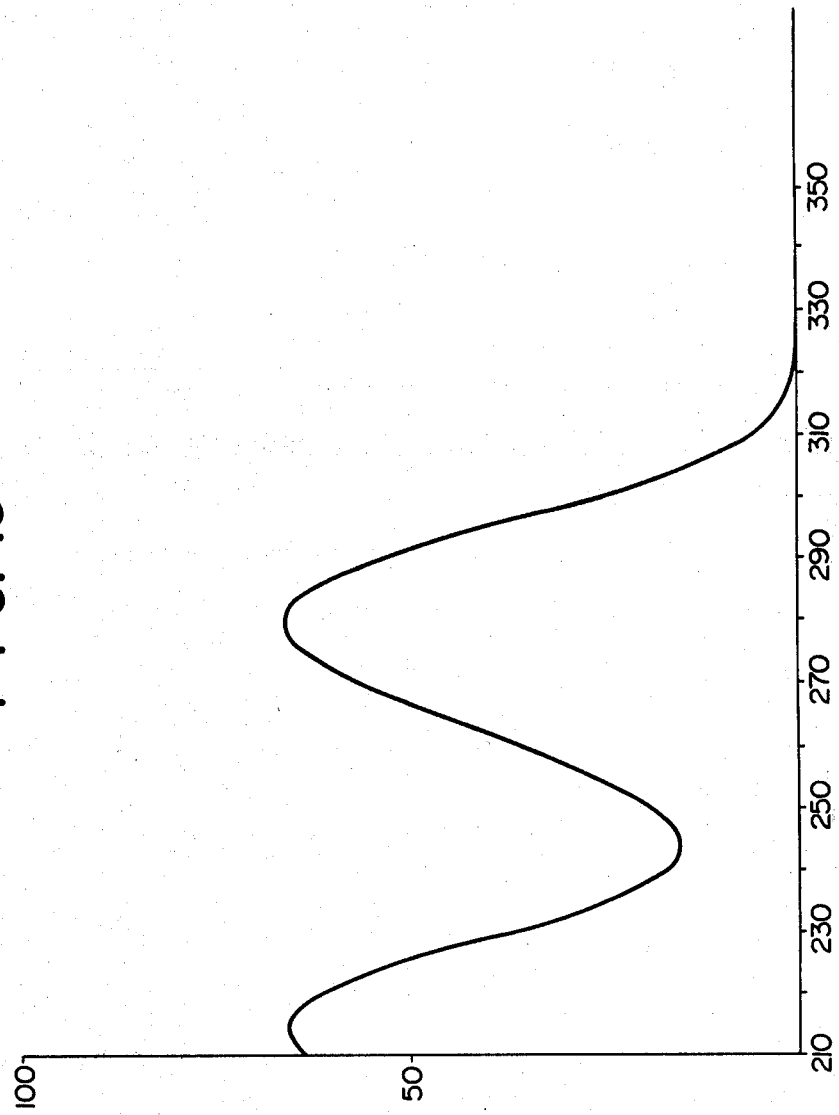
Figure 14:
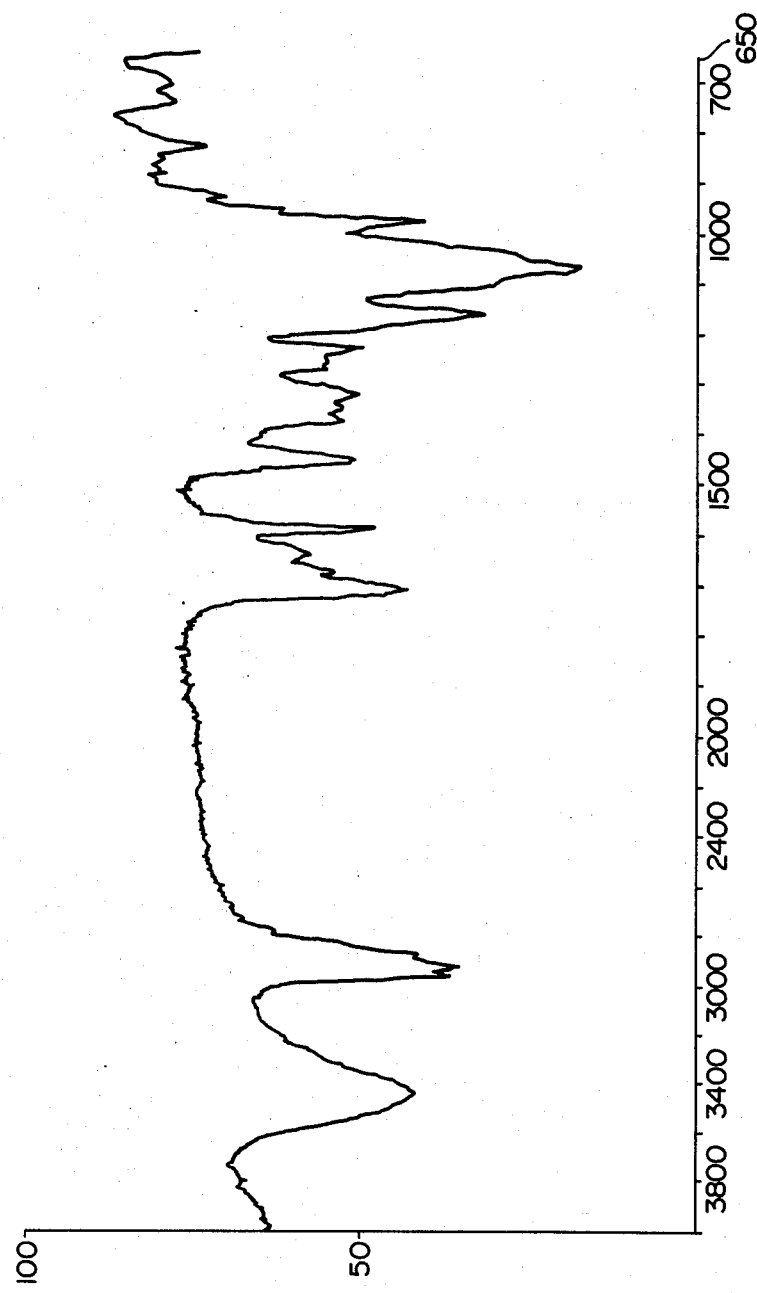
Figure 15:
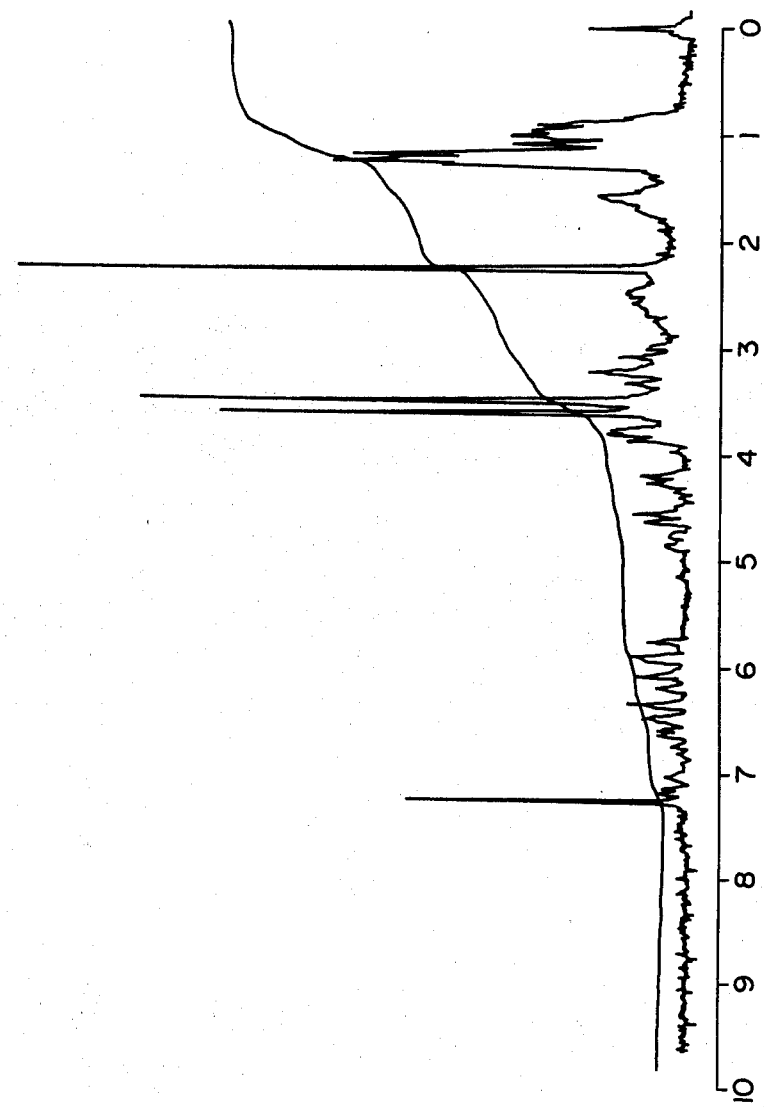

In the accompanying drawings:

FIG. 1 and FIG. 2 show infra-red absorption spectra of the novel antibiotic substances of the present invention A 11725 I and II, respectively;

FIG. 3 and FIG. 4 ultra-violet absorption spectra of the antibiotic substances A 11725 I and II, respectively;

FIG. 5 and FIG. 6 nuclear magnetic resonance spectra of the antibiotic substances A 11725 I and II, respectively;

FIG. 7 ultra-violet absorption spectrum of the antibiotic substance A 11725 III;

FIG. 8 infra-red absorption spectrum of the antibiotic substance A 11725 III;

FIG. 9 nuclear magnetic resonance spectrum of the antibiotic substance A 11725 III;

FIG. 10 ultra-violet absorption spectrum of the antibiotic substance A 11725 Ia;

FIG. 11 infra-red absorption spectrum of the antibiotic substance A 11725 Ia;

FIG. 12 nuclear magnetic resonance spectrum of the antibiotic substance A 11725 Ia;

FIG. 13 ultra-violet absorption spectrum of the antibiotic substance A 11725 IIa;

FIG. 14 infra-red absorption spectrum of the antibiotic substance A 11725 IIa; and FIG. 15 nuclear magnetic resonance spectrum of the antibiotic substance A 11725 IIa.

The antibiotic substances A 11725 I, II, III, Ia and IIa provided by the present invention are found to have the physico-chemical properties as shown in Table 1.

From these various properties, the present compounds are judged to be the antibiotic substances belonging to the group of basic macrolides. Since there are known none of such compounds in the art, each of these compounds is judged to be novel compound.

More specifically, while their structural formulas are not precisely known yet, some specific features of these compounds as estimated from analysis of the data as compared with those of known ones have been elucidated so far. Namely, all of these compounds are 16-membered cyclic macrolide type substances, having attached to said ring saccharide groups of desosamine and 6-deoxy-2,3-di-o-methyl-hexose (except for the substance A 11725 III which has desosamine and 6-deoxy-(2 or 3)-o-methyl-hexose), respectively. There is no aldehyde group bound in the molecules of these compounds. Furthermore, the antibiotics A 11725 I and II are estimated to have the following partial structure:

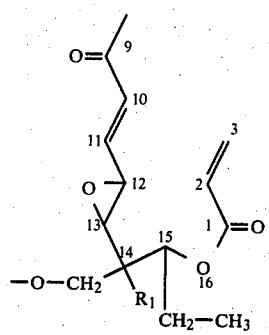

wherein $R_1$ is hydrogen atom for the antibiotic A 11725 I and hydroxyl group for the antibiotic A 11725 II. The antibiotics A 11725 III, Ia and IIa are also estimated to have the following partial structure:

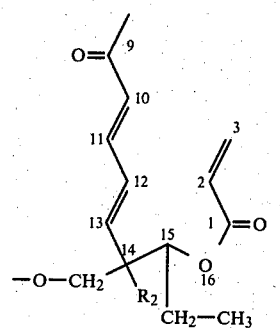

wherein $R_2$ is hydrogen atom for the antibiotics A 11725 III and Ia and hydroxyl group for the antibiotic A 11725 IIa.

TABLE 1

|  | A 11725 I | A 11725 II | A 11725 III | A 11725 Ia | A 11725 IIa |
|---|---|---|---|---|---|
| Appearance: | white powders | white powders | white powders | white crystals | white crystals |
| Molecular formula: | $C_{37}H_{61}NO_{12}$ | $C_{37}H_{61}NO_{13}$ | $C_{36}H_{59}NO_{11}$ | $C_{37}H_{61}NO_{11}$ | $C_{37}H_{61}NO_{12}$ |
| Elemental analysis: |  |  |  |  |  |
| Found: C | 62.34 | 60.57 | 63.25 | 64.05 | 62.21 |
| H | 9.25 | 8.95 | 9.01 | 9.10 | 8.82 |
| N | 1.96 | 1.96 | 2.10 | 2.04 | 1.94 |
| Calculated: C | 62.43 | 61.05 | 63.41 | 63.86 | 62.43 |
| H | 8.64 | 8.44 | 8.72 | 8.84 | 8.64 |
| N | 1.97 | 1.92 | 2.05 | 2.01 | 1.97 |
| Molecular weight (measured by mass spectrum): | 711 | 727 | 681 | 695 | 711 |
| Melting point(or | | | | | |

TABLE 1-continued

|  | A 11725 I | A 11725 II | A 11725 III | A 11725 Ia | A 11725 IIa |
|---|---|---|---|---|---|
| decomposition point: | 103–107° C. | 102–106° C. | 99–102° C. | 174–176° C. | 148–150° C. |
| $[\alpha]_D$: | −40.0° (C = 1, methanol) | −31.0° (C = 1, methanol) | −2.3° (C = 1.0, methanol) | +2.7° (C = 1.0, methanol) | +18.7° (C = 1.0, methanol) |
| Ultraviolet absorption spectrum: | FIG. 3 (25γ/ml, in methanol) | FIG. 4 (25γ/ml, in methanol) | FIG. 7 (28γ/ml, in methanol) | FIG. 10 (23γ/ml, in methanol) | FIG. 13 (20.42γ/ml, in methanol) |
|  | λmax217mm ($E_{1cm}^{1\%}$ = 340) | λmax217mm ($E_{1cm}^{1\%}$ = 337) | λmax216mm ($E_{1cm}^{1\%}$ = 310) | λmax215mm ($E_{1cm}^{1\%}$ = 326.1) | λmax215mm ($E_{1cm}^{1\%}$ = 323.2) |
|  | λmax240mm (sh, 180) | λmax240mm (sh, 180) | λmax283mm ($E_{1cm}^{1\%}$ = 310) | λmax283mm ($E_{1cm}^{1\%}$ = 333.9) | λmax280mm ($E_{1cm}^{1\%}$ = 323.2) |
| Infra-red absorption spectrum (KBr method): | FIG. 1 (having absorption bands at wavelengths around 3440,2960 2920,2875 2845,2780 1715,1685 1650,1645 1620,1460 1375,1355 1325,1275 1255,1230 1170,1110 1080,1045 980, 955 930, 885 855, 830cm$^{-1}$) | FIG. 2 (having absorption bands at wavelengths around 3460,2960 2930,2880 2830,2780 1715,1690 1645,1620 1455,1375 1350,1325 1270,1255 1230,1165 1110,1075 1040,980 955, 930 885, 855 830cm$^{-1}$) | FIG. 8 (having absorption bands at wavelengths around 3600,2970 2930,2880 1710,1675 1645,1590 1460,1380 1350,1320 1275,1230 1170,1070 1050,980 960, 930 835, 750cm$^{-1}$) | FIG. 11 (having absorption bands at wavelengths around 3600,2970 2930,2880 2830,2780 1720,1710 1678,1645 1625,1596 1460,1380 1350,1322 1275,1258 1230,1165 1105,1072 1045,980 960, 930 882, 858 830cm$^{-1}$) | FIG. 14 (having absorption bands at wavelengths around 3550,2970 2930,2880 1830,2780 1720,1710 1670,1640 1590,1450 1375,1345 1320,1270 1250,1230 1160,1120 1100,107, 1040,980 955, 925 880, 850 710cm$^{-1}$) |
| Nuclear magnetic resonance (CDCl$_3$, 100MHz, TMS) | FIG. 5 | FIG. 6 | FIG. 9 | FIG. 12 | FIG. 15 |
| TLC silica gel (Merck Co., No. 5714): |  |  |  |  |  |
| CHCl$_3$: methanol (5:1) | 0.48 | 0.40 | 0.40 | — | — |
| CHCl$_3$: methanol: 7% ammonia (40:12:20, lower layer) | 0.72 | 0.56 | — | — | — |
| Methanol: Benzene: Acetone (1:1) | — | — | 0.31 0.05 | — | — |
| n-butanol-acetic acid-water (3:1:1) | — | — | 0.59 | — | — |
| Coloration reaction: Discoloration of aqueous potassium permanganate solution: | + | + | + | + | + |
| Ninhydrin reaction, Sakagushi's |  |  |  |  |  |

TABLE 1-continued

|  | A 11725 I | A 11725 II | A 11725 III | A 11725 Ia | A 11725 IIa |
|---|---|---|---|---|---|
| reaction, ferric chloride reaction: | — | — | — | — | — |
| Acidic or basic nature: | Basic | Basic | Basic | Basic | Basic |
| Solubility: | Soluble in acidic water and organic solvents such as methanol acetone, ethyl acetate, benzene etc.; difficultly soluble in basic water | Similar to A 11725 I | Soluble in acidic water, methanol, acetone, ethyl acetate and benzene; difficultly soluble in basic water; insoluble in hexane | Similar to A 11725 III | Similar to A 11725 III |

The antibiotic substances of the present invention are also found to have the anti-bacterial or anti-mycoplasmal spectra as shown in Table 2, as measured by agar dilution method.

The substances provided by the present invention can be used in the form of pharmaceutically acceptable salts generally used with mineral acids, organic acids, etc., for example, tartaric acid salts, citric acid salts, succinic acid salts, and the like.

The antibiotic substances of the present invention can be administered orally in the form of tablets and powders, or alternatively also by way of intravenous injection. The dosage may sufficiently about 400 to 2000 mg per adult human per day so as to be effective against respiratory infectious diseases caused by Gram-positive microorganisms such as Staphylococcus. When toxicity is measured for the antibiotic substances of the present invention, $LD_{50}$ in case of mouse is found to be as much as 2,000 mg or more by oral administration. The present substances can also be utilized as antibiotic substances to be added in fodders and as antibiotic substances for therapy of animals.

TABLE 2

| Test microorganisms | $10^8$ x1 | Minimum growth inhibitory concentration mcg/ml | | | | |
|---|---|---|---|---|---|---|
| | | A 11725 I | A 11725 II | A 11725 III | A 11725 Ia | A 11725 IIa |
| 1. Staphylococcus aureus (ATCC 6538 P) | | 0.2 | 0.2 | 0.2 | 0.1 | 0.4 |
| 2. Staphylococcus aureus (MS 353) | | 0.2 | 0.2 | 0.2 | 0.1 | 0.4 |
| 3. Staphylococcus aureus (MS 353 C36) | | ≦0.05 | 0.1 | 0.2 | ≦0.5 | 0.2 |
| 4. Staphylococcus aureus (MS 353 AO) | | >100 | >100 | >100 | >50 | >100 |
| 5. Staphylococcus aureus (0116) | | >100 | >100 | 100 | >50 | >100 |
| 6. Staphylococcus aureus (0119) | | >100 | >100 | >100 | >50 | >100 |
| 7. Staphylococcus aureus (0126) | | | | | 0.8 | 0.8 |
| 8. Staphylococcus aureus (0127) | | >100 | >100 | >100 | >50 | >100 |
| 9. Staphylococcus epidermidis (s.p.-al-l) | | 0.1 | 0.1 | 0.1 | ≦0.05 | 0.2 |
| 10. Streptococcus pyogenes (N.Y.5) | | ≦0.05 | ≦0.05 | 0.1 | ≦0.025 | ≦0.05 |
| 11. Streptococcus pyogenes (1022) | | >100 | >100 | >100 | >50 | >100 |
| 12. Streptococcus faecalis (1501) | | >100 | >100 | >100 | >50 | >100 |
| 13. Streptococcus agalactiae (1020) | | 12.5 | 6.3 | 25 | 25 | 25 |
| 14. Sarcina lutea (ATCC 9341) | | ≦0.05 | ≦0.05 | ≦0.05 | ≦0.025 | ≦0.05 |
| 15. Micrococcus flavus (ATCC 10240) | | ≦0.05 | 0.2 | ≦0.05 | 0.1 | 0.1 |
| 16. Corynebacterium diphtheriae (P.W.8) | | 0.4 | 0.4 | 3.1 | 1.6 | 3.1 |
| 17. Bacillus subtilis (ATCC 6633) | | 0.4 | 0.4 | 1.6 | 0.4 | 1.6 |
| 18. Escherichia coli (NIHJ-JC2) | | >100 | >100 | >100 | >50 | >100 |
| 19. Escherichia coli (B) | | 100 | 25 | >100 | >50 | >100 |
| 20. Klebsiella pneumoniae (ATCC 10031) | | 25 | 25 | 100 | >50 | 50 |
| 21. Salmonella typhosa | | | | | | |

TABLE 2-continued

| Test microorganisms | 10⁸ x1 | A 11725 I | A 11725 II | A 11725 III | A 11725 Ia | A 11725 IIa |
|---|---|---|---|---|---|---|
| (E 901) | | >100 | >100 | >100 | >50 | >100 |
| 22. Salmonella enteritidis gertner | | >100 | >100 | >100 | >50 | >100 |
| 23. Shigella flexneri type 3a | | 100 | 50 | >100 | >50 | >100 |
| 24. Shigella sonney (E 33) | | >100 | >100 | >100 | >50 | >100 |
| 25. Proteus vulgaris (OX19) | | 100 | 50 | 100 | >50 | >100 |
| 26. Serratia marcescence | | >100 | >100 | >100 | >50 | >100 |
| 27. Pseudomonas aeruginosa (IAM 1095) | | >100 | >100 | >100 | >50 | >100 |
| 28. Mycoplasma gallisepticum | | 0.006 | 0.03 | | 0.03 | 0.03 |
| 29. Mycoplasma synoviae | | 0.03 | 0.8 | | 0.8 | 0.8 |

The antibiotic substances according to the present invention can be produced by biological method. There is used in the present invention an actinomycete belonging to genus Micromonospora, which is called as "Micromonospora sp. A 11725" and has been isolated from the soil in a potato farm in Unazuki-cho, Shimoshinkawa-gun, Toyama prefecture, Japan (FERM-P No. 4488, deposited at Institute of Fermentation Research, Agency of Industry and Technology, Japan; NRRL 11452, deposited on March 21, 1979).

The microorganism to be used in the present invention has the following microbiological properties:

I. Morphological properties

Substrate mycelium is elongated, wavy, simply branched, 0.6 to 0.8μ in diameter, no fragmentation of mycelium being observed. There is formed one spore per each short sporophore at its tip which is grown from substrate mycelium, said spore being spherical to oval with a size of 1.0 to 1.5μ, having thorn-like projections, thus giving a confetti-like appearance. On agar medium, depending on its composition, undergrown aerial mycelium may sometimes be formed, or black spore layer may also be formed on colony surface.

II. Growth on various media

Table 3 shows the results of observation made on the cultured products on various media after cultivation at 30° C. for 20 days. The indication of the colors follows the classification of colors according to Color Harmony Manual, 4th ed., 1958, Container Corporation of America.

TABLE 3

Growth on various media

| Medium | Growth | Color of substrate mycelium | Spore layer | Undergrown aerial mycelium | Soluble pigment |
|---|---|---|---|---|---|
| Sucrose-nitrate agar | Good | Cedar(6le) to Brick Red(6ng) | None | Poor; Flesh Pink (5ca) Dusty Peach (5ec) | Dusty Coral (6gc) to Redwood (6ie) |
| Glucose-asparagine (Waksman No. 2)* | Trace to Poor | Nude Tan (4gc) | None | None | None |
| Glycerol-asparagine agar | Trace | Nude Tan (4gc) to Bisque (4ec) | None | None | None |
| Starch-inorganic salts agar | Moderate to good | Brick Red(5ng) | Moderate; Lamp Black(p) | None | None |
| Tyrosine agar | Trace | Bisque (3ec) to Beige (3gc) | Trace; Lamp Black(p) | None | None |
| Oatmeal agar | Good to moderate | Brick Red(5ng) to Copper Brown (5pi) | Good; Lamp Black(p) | None | Copper Tan (5ie) is formed around colony |
| Yeast-malt agar | Good | Light Rose Brown (7lg) to Rose Brown (7ni) | Trace; Lamp Black(p) | None | Cedar(6le) is slightly formed |
| Glucose-yeast extract agar (Waksman | Moderate | Cocoa Brown (5lg) to Dark Redwood | Poor to trace; Lamp Black(p) | Trace; Shell Pink (5ba) | None |

TABLE 3-continued

| Medium | Growth | Color of substrate mycelium | Spore layer | Under-grown aerial mycelium | Soluble pigment |
|---|---|---|---|---|---|
| No. 29)* Glucose-nitrate agar (Waksman No. 1)* | Moderate to poor | (6lg) Cedar (6½le) to Brick Red (6½ng) | None | None | None |
| Nutrient agar | Trace | Color-less to Light Tan(3gc) | Trace; Lamp Black(p) | None | None |
| Emerson's agar (Waksman No. 28)* | Good, wrinkled | Cedar (6le–6½le) | None | None | None |
| Bennett's agar (Waksman No. 30)* | Moderate to good | Light Rose Brown (7lg) to Rose Brown(7ni) | Moderate; Lamp Black(p) | None | Light Rose Brown(7lg) to Rose Brown(7ni) is formed around colony |
| Hickey-Tresner's agar (Waksman No. 32)* | Good | Cocoa Brown (5lg) | None | Poor; Bisque (4ec) | Cedar(6lg) is formed around colony |
| Starch-NZ amine-yeast extract agar (ATCC No. 172)** | Good | Dark Wine (8pi) to Mauve Wine (8ni) | Good; Lamp Black(p) | None | Old Wine (8ng) |
| Glucose-NZ amine agar (1% glucose, 3% NZ amine type A, 1.5% agar) | Moderate to poor | Cedar (6le) to Rust Tan (5le) | None | None | None |
| Glucose-peptone agar | Moderate | Rose Brown (7ni) | Moderate to poor; Lamp Black(p) | None | Old Wine (7ng) |
| Potato slice (Waksman No. 40)* | No growth to trace | | | | |
| Potato slice + CaCO₃ (7pn) | Good, wrinkled | Dark Rose Brown | Moderate; Lamp Black(p) slightly | None | Dark Rose Brown (7pn) formed |
| Peptone-yeast-iron agar | Trace to poor | Light Tan (3gc) | Trace; Lamp Black(p) | None | None |

*Waksman, S.A. "The Actinomycetes" Vol. 2 1961 p. 327-334, Williams & Wilkins Co.
**The American Type Culture Collection, Catalogur of Strains 18th ed., 1968 p. 142

III. Physiological properties (1) Assimilability of carbon sources:
  Assimilable:
    D-arabinose, D-glucose, D-fructose, D-mannose, sucrose, trehalose, starch
  Slightly assimilable:
    L-arabinose, D-cellobiose, D-ribose
  Not assimilable:
    D-galactose, β-lactose, D-melezitose, α-melibiose, raffinose, L-rhamnose, L-sorbose, D-xylose, glycerol, salicin, dulcitol, inositol, D-mannitol, D-sorbitol, cellulose (Because the present microorganism can be grown only poorly on Pridham-Gottlieb agar medium containing D-glucose, a medium containing 0.5% yeast extract and 1.5% agar is used as the basal medium.)

(2) Growth temperature range: 15°–45° C.
(3) Liquefaction of gelatin: liquefied in glucose-peptone-gelatin medium
(4) Hydrolysis of starch: hydrolyzed on starch-inorganic salts agar medium
(5) Skimmed milk: peptonized and coagulated
(6) Production of melanoids pigment: not produced on tyrosine agar and peptone-yeast-iron agar (7) Salt resistance (according to the method written in Inter. J. System. Bacteriol. 21, 240–247, 1971):

| NaCl conc. % | Growth |
| --- | --- |
| 0 | good |
| 1.5 | moderate to good |
| 3.0 or more | no growth |

(8) Decomposition of cellulose: not decomposed (9) Production of nitrite (using the organic medium described in Inter. J. System. Bacteriol., 21, 240–247, 1971): not produced As described above, the strain A 11725 has spores each individually grown at the tip of sporophore produced from branched substrate mycelium, does not produce intrinsic aerial mycelium and is a mesophilic microorganism. Therefore, it is a microorganism belonging to the genus Micromonospora.

For the reasons set forth above, the strain A 11725 is named as Micromonospora sp. A 11725.

The antibiotic substances A 11725 I to III can be produced by culturing the above strain Micromonospora sp. A 11725 in a medium containing ingredients conventionally used for cultivation of microorganisms under aerobic conditions and then separating by extraction the antibiotic substances accumulated in the cultured product. The antibiotic substances A 11725 Ia and IIa can be derived by chemical modification of the thus prepared antibiotic substances A 11725 I and II, respectively, with a suitable chemical reagent.

As the cultural medium, there may be used either solid or liquid medium. For production on a large scale, a liquid medium, especially an aqueous medium is preferred. Referring to the components in the medium, there may suitably be used as carbon source glucose, starch, glycerine, sucrose, molasses, dextrin, and the like. As nitrogen source, peptone, meat extract, soybean powders and hydrolyzed casein are suitable. But cottonseed dregs, corn steep liquor, nitrates and ammonium salts may also be utilized. There may also be used other inorganic substances containing cations such as sodium, potassium, magnesium, calcium, cobalt, manganese and iron, and(or) those containing anions such as chlorine, sulfuric acid, phosphoric acid and acetic acid. Further, for promoting growth of microorganisms, dried yeast and yeast extract may also be used. For the purpose of adjusting pH of the medium, calcium carbonate may be added thereto. In addition, in order to suppress foaming during cultivation, there may be added a suitable amount of defoaming agent such as silicone resin, animal or vegetable oil, etc. The medium which is particularly suitable for practicing the method according to the present invention is a medium which contains glucose, dextrin, defatted soybean powders, calcium carbonate and cobalt chloride as medium components.

Cultivation may be carried out under conditions conventionally used for production of antibiotic substances. The cultivation temperature may range from 20° to 37° C., preferably from 26° to 30° C. The cultivation days, which may vary depending on the cultural conditions, are generally 4 to 5 days.

While any conventionally known cultivation method may be used in the present invention, it is suitable from standpoint of a large scale production to effect cultivation under aeration with stirring in a fermentation tank. As the most suitable method for separating and collecting the antibiotic substances A 11725 I, II and III from the cultured product, microorganism cells and other solid substances are first removed by filtration or centrifugation and the filtrate is then subjected to extraction by the extraction method using an organic solvent. As organic solvents to be used for extraction, there may be mentioned chlorinated hydrocarbons such as chloroform, dichloroethylene, trichloroethylene, etc. and aliphatic acid esters such as ethyl acetate, butyl acetate, amyl acetate, etc. There may also be used other organic solvents which can well dissolve the substances A 11725 I, II and III and are hardly miscible with water.

The organic solvent extract containing the substances A 11725 I, II and III can be concentrated by evaporation under reduced pressure to 1/100 to 1/200 of its volume, which concentrate is in turn adjusted to pH 1.0 to 3.0 with an acid such as hydrochloric acid, sulfuric acid or acetic acid, followed by separation of the aqueous layer, then adjusted to pH 7.8 to 9.0 with an alkaline solution such as caustic soda, caustic potash or ammonia and further subjected to extraction with an organic solvent again. By concentration of this extract by evaporation of the solvent under reduced pressure to dryness, there is obtained the crude product containing the substances A 11725 I, II and III. The crude product is fractionated by such a method as column chromatography using silica gel or counter-current distribution. Each fraction is subjected to silica gel thin layer chromatography to detect the component contained therein. The fractions containing pure A 11725 I, II and III, respectively, are collected and evaporated under reduced pressure to dryness to give white powders of objective compounds, respectively.

Referring to the typical method for preparation of the substances A 11725 Ia or IIa, the substance A 11725 I or II as prepared by the method described above is dissolved in a lower aliphatic acid such as glacial acetic acid or propionic acid. Then, under cooling, chromous chloride is added to the solution and the reaction is conducted at room temperature for 3 to 20 hours. The chromous chloride may be used in an amount of two moles or more per mole of the substance A 11725 I or II. The reaction product is then poured into water or ice-water and the resultant solution is made weakly basic to about pH 8.5 with a basic compound such as sodium carbonate before it is extracted with a solvent such as ethyl acetate or benzene. The extract is washed, dried and evaporated to remove the solvent under reduced pressure, whereby crude powders are obtained. The crude powders are purified by silica gel chromatography using an eluant comprising chloroform-methanol-28% ammonia (400:10:1) to give the substances A 11725 Ia or IIa. In the thus prepared substances A 11725 Ia and IIa, there are formed double bonds in the molecule which are formed by converting the epoxy groups in the molecule of the substances A 11725 I and II, respectively.

The present invention is explained in further detail with reference to the following Examples, by which the present invention is not limited.

EXAMPLE 1

Preparation of antibiotic substance A 11725-I, A 11725-II and A 11725-III:

In an Erlenmeyer's flask of 500 ml capacity was apportioned 100 ml of a medium (pH 7.0) containing 1% dextrin, 1% glucose, 0.5% hydrolyzed casein, 0.5% yeast extract and 0.1% calcium carbonate and the medium was sterilized by heating at 120° C. for 20 minutes. To each of ten ampoules containing this medium was inoculated one platinum loop of culture broth of Micromonospora sp. A 11725 strain cultivated on slant agar, and shaking cultivation was carried out at 30° C. for 120 hours. These seed cultures were transplanted in a jar fermenter containing 20 liters of the heat-sterilized medium having the same composition and cultivation was carried out at 30° C. under aseptic aeration of 20 liters per minute with stirring at 300 r.p.m. for 72 hours. Subsequently, 10 liters of the above culture broth were transplanted into a tank of 250 liter capacity containing 200 liters of heat-sterilized medium (pH 7.2) containing 5% dextrin, 0.5% glucose, 3% defatted soybean powders and 0.2% calcium carbonate, and cultivation was carried out at 30° C. under aseptic aeration of 100 liter per minute with stirring at 250 r.p.m. for 120 hours to give 190 liters of cultured product.

The above cultured product (190 liter) was filtered to remove microorganism cells and other solids, whereby 160 liters of filtrate were obtained. This filtrate was subjected to extraction with the same quantity of ethyl acetate, whereby 160 liters of ethyl acetate solution containing the objective compounds were obtained. Said solution was concentrated under reduced pressure to 50 liters, which were in turn mixed with 20 liters of an aqueous hydrochloric acid solution of pH 2.5 to be transferred into the aqueous layer through phase transfer. Further, the aqueous hydrochloric acid solution was adjusted to pH 8.5 with concentrated ammonia and subjected to extraction with 20 liters of chloroform. The chloroform layer was concentrated to dryness to give 8.5 g of crude product.

The above crude product (8.5 g) was dissolved in 50 ml of chloroform and the resultant solution was adsorbed on a silica gel column (3 cm×55 cm) previously filled with chloroform. Then, it was developed with a solvent comprising chloroform-methanol-28% ammonia (20:1:0.1) into fractions of each 15 ml. The objective compound contained in each fraction was detected by anti-bacterial activity using *Bacillus subtilis* and thin-layer chromatography using chloroform-methanol-7% ammonia (40:12:20:lower layer) as developing solvent and the fractions containing the same compound were collected.

The fractions from No. 61 to No. 78 were found to contain only the substance identified as A 11725 I and these fractions were concentrated to dryness to obtain 1.2 g of A 11725 I. The fractions from No. 126 to No. 160 were found to contain only the substance identified as A 11725 II and these fractions were concentrated to dryness to obtain 1.7 g of A 11725 II. The fractions from No. 241 to No. 320 were found to contain only the substance identified as A 11725 III and these fractions were concentrated to to dryness to obtain 0.2 g of A 11725 III.

EXAMPLE 2

Preparation of antibiotic substance A 11725 Ia

One gram of the antibiotic substance A 11725 I prepared in the same manner as described in Example 1 was dissolved in 30 ml of glacial acetic acid and then 1.0 g of chromous chloride was added to the resultant solution under cooling. The reaction was carried out at room temperature with stirring for 16 hours. Then, the reaction mixture was poured into 700 ml of ice-water. After the solution was adjusted with an aqueous sodium carbonate solution to pH 8.5, it was extracted with 400 ml of ethyl acetate three times. The ethyl acetate layers were combined and washed with water, dried with sodium sulfate. The dried product was thereafter evaporated under reduced pressure to dryness to give about 800 mg of crude solid containing A 11725 Ia. The crude solid was then subjected to elution through silica gel column (2.4×55 cm) using chloroform-methanol-28% ammonia (400:10:1) as eluant into fractions of each 15 ml. The fractions from No. 130 to No. 210 were combined, followed by concentration under reduced pressure to dryness, to obtain 605 mg of purified A 11725 Ia.

EXAMPLE 3

Preparation of antibiotic substance 11725 IIa

Example 2 was repeated except that the substance A 11725 II prepared in the same manner as described in Example 1 was used in place of the substance A 11725 I. From the silica gel column, the fractions from No. 150 to No. 220 were recovered to obtain 612 mg of purified A 11725 IIa.

We claim:

1. A novel antibiotic substance A 11725 I or a pharmaceutically acceptable salt thereof having the following properties:
    Appearance: white powders;
    Molecular formula: $C_{37}H_{61}NO_{12}$;
    Molecular weight: 711;
    Melting point: 103° to 107° C.;
    $[\alpha]_D$: −40.0° (C=1, methanol);
    Ultra-violet absorption spectrum: as shown in FIG. 3;
    Infra-red absorption spectrum: as shown in FIG. 1;
    Nuclear magnetic resonance spectrum: as shown in FIG. 5;
    Coloration reaction:
        Discoloration of aqueous potassium permanganate solution: +;
        Ninhydrin reaction, Sakaguchi's reaction and ferric chloride reaction: −;
    Acid or basic nature: Basic;
    Solubility: soluble in acidic water, methanol, acetone, ethyl acetate and benzene, difficulty soluble in basic water.

2. A novel antibiotic substance A 11725 II or a pharmaceutically acceptable salt thereof having the following properties:
    Appearance: white powders;
    Molecular formula: $C_{37}H_{61}NO_{13}$;
    Molecular weight: 727;
    Melting point: 102° to 106° C.; ;P1 $[\alpha]_D$: −31.0° (C=1, methanol);
    Ultra-violet absorption spectrum: as shown in FIG. 4;
    Infra-red absorption spectrum: as shown in FIG. 2;
    Nuclear magnetic resonance spectrum: as shown in FIG. 6;
    Coloration reaction:
        Discoloration of aqueous potassium permanganate solution: +;
        Ninhydrin reaction, Sakaguchi's reaction and ferric chloride reaction: −;
    Acidic or basic nature: Basic;
    Solubility: soluble in acidic water, methanol, acetone, ethyl acetate and benzene, difficulty soluble in basic water.

3. A novel antibiotic substance A 11725 III or a pharmaceutically acceptable salt thereof having the following properties:
    Appearance: white powders;

Molecular formula: $C_{36}H_{59}NO_{11}$;
Molecular weight: 681;
Melting point: 99°-102° C.;
$[\alpha]_D$: −2.3° (C=1.0, methanol);
Ultra-violet absorption spectrum: as shown in FIG. 7;
Infra-red absorption spectrum: as shown in FIG. 8;
Nuclear magnetic resonance spectrum: as shown in FIG. 9;
Coloration reaction:
  Discoloration of aqueous potassium permanganate solution: +;
  Ninhydrin reaction, Sakaguchi's reaction and ferric chloride reaction: −;
Acidic or Basic nature: Basic;
Solubility: soluble in acidic water, methanol, acetone, ethyl acetate and benzene, difficulty soluble in basic water and insoluble in hexane.

4. A novel antibiotic substance A 11725 Ia or a pharmaceutically acceptable salt thereof having the following properties:
Appearance: white crystals;
Molecular formula: $C_{37}H_{61}NO_{11}$;
Molecular weight: 695;
Melting point: 174° to 176° C.;
$[\alpha]_D$: +2.7° (C=1.0, methanol);
Ultra-violet absorption spectrum: as shown in FIG. 10;
Infra-red absorption spectrum: as shown in FIG. 11;
Nuclear magnetic resonance spectrum: as shown in FIG. 12;
Coloration reaction:
  Discoloration of aqueous potassium permanganate solution: +;
  Ninhydrin reaction, Sakaguchi's reaction and ferric chloride reaction: −;
Acidic or basic nature: Basic;
Solubility: soluble in acidic water, methanol, acetone, ethyl acetate and benzene, difficulty soluble in basic water and insoluble in hexane.

5. A novel antibiotic substance A 11725 IIa or a pharmaceutically acceptable salt thereof having the following properties:
Appearance: white crystals;
Molecular formula: $C_{37}H_{61}NO_{12}$;
Molecular weight: 711;
Melting point: 148° to 150° C.;
$[\alpha]_D$: +18.7° (C=1.0, methanol)
Ultra-violet absorption spectrum: as shown in FIG. 13;
Infra-red absorption spectrum: as shown in FIG. 14;
Nuclear magnetic resonance spectrum: as shown in FIG. 15;
Coloration reaction:
  Discoloration of aqueous potassium permanganate solution: +;
  Ninhydrin reaction, Sakaguchi's reaction and ferric chloride reaction: −;
Acidic or basic nature: Basic;
Solubility: soluble in acidic water, methanol, acetone, ethyl acetate and benzene, difficulty soluble in basic water and insoluble in hexane.

6. A process for producing antibiotic substances, which comprises culturing Micromonospora sp. A 11725 (NRRL 11452) which is capable of producing at least one of the antibiotic substances A 11725 I, II and III in a medium containing an assimilatable carbon source, a nitrogen source and an inorganic substance under aerobic conditions to accumulate said antibiotic substances in said medium and then collecting and isolating the accumulated antibiotic substances by separation from the cultured product, said antibiotic substance A 11725 I having the following properties:
Appearance: white powders;
Molecular formula: $C_{37}H_{61}NO_{12}$;
Molecular weight: 711;
Melting point: 103° to 107° C.;
$[\alpha]_D$: −40.0° (C=1, methanol);
Ultra-violet absorption spectrum: as shown in FIG. 3;
Infra-red spectrum: as shown in FIG. 1;
Nuclear magnetic resonance spectrum: as shown in FIG. 5;
Coloration reaction:
  Discoloration of aqueous potassium permanganate solution: +;
  Ninhydrin reaction, Sakaguchi's reaction and ferric chloride reaction: −;
Acid or basic nature: Basic;
Solubility: soluble in acidic water, methanol, acetone, ethyl acetate and benzene, difficulty soluble in basic water;
said antibiotic substance A 11725 II having the following properties:
Appearance: white powders;
Molecular formula: $C_{37}H_{61}NO_{13}$;
Molecular weight: 727;
Melting point: 102° to 106° C.;
$[\alpha]_D$: −31.0° (C=1, methanol);
Ultra-violet absorption spectrum: as shown in FIG. 4;
Infra-red absorption spectrum: as shown in FIG. 2;
Nuclear magnetic resonance spectrum: as shown in FIG. 6;
Coloration reaction:
  Discoloration of aqueous potassium permanganate solution: +;
  Ninhydrin reaction, Sakaguchi's reaction and ferric chloride reaction: −;
Acidic or basic nature: Basic;
Solubility: soluble in acidic water, methanol, aceton, ethyl acetate and benzene, difficulty soluble in basic water;
and the antibiotic substance A 11725 III having the following properties:
Appearance: white powders;
Molecular formula: $C_{36}H_{59}NO_{11}$;
Molecular weight: 681;
Melting point: 99°-102° C.;
$[\alpha]_D$: −2.3° (C=1.0, methanol);
Ultra-violet absorption spectrum: as shown in FIG. 7;
Infra-red absorption spectrum: as shown in FIG. 8;
Nuclear magnetic resonance spectrum: as shown in FIG. 9;
Coloration reaction:
  Discoloration of aqueous potassium permanganate solution: +;
  Ninhydrin reaction, Sakaguchi's reaction and ferric chloride reaction: −;
Acidic or Basic nature: Basic;
Solubility: soluble in acidic water, methanol, aceton, ethyl acetate and benzene, difficulty soluble in basic water and insoluble in hexane.

7. A process according to claim 6, wherein all of the substances A 11725 I, II and III are produced and accumulated within said medium and are thereafter separated and isolated by fractionation into each individual antibiotic substance.

8. A process according to claim 6, wherein cultivation is effected at a temperature ranging from 20° to 37° C. in a period of from four to five days in an aqueous medium.

9. A process for producing antibiotic substances, which comprises culturing Micromonospora sp. A 11725 (NRRL 11452) in a culture medium containing an assimilatable carbon source, a nitrogen source and an inorganic substance under aerobic conditions to produce and to accumulate at least one antibiotic substance A 11725 I and A 11725 II within said medium, then isolating the thus-accumulated at least one antibiotic substance by separation from the culture medium and thereafter reacting either the antibiotic substance A 11725 I or the antibiotic substance A 11725 II with a chemical reagent which can convert epoxy groups in the molecule of said substance to double bonds to produce either an antibiotic substance A 11725 Ia or an antibiotic substance A 11725 Ia, respectively, said antibiotic substance A 11725 Ia having the following properties:

Appearance: white crystals;
Molecular formula: $C_{37}H_{61}NO_{11}$;
Molecular weight: 695;
Melting point: 174° to 176° C.;
$[\alpha]_D$: +2.7° (C=1.0, methanol);
Ultra-violet absorption spectrum: as shown in FIG. 10;
Infra-red absorption spectrum: as shown in FIG. 11;
Nuclear magnetic resonance spectrum: as shown in FIG. 12;
Coloration reaction:
   Discoloration of aqueous potassium permanganate solution: +;
   Ninhydrin reaction, Sakaguchi's reaction and ferric chloride reaction: —;
Acidic or basic nature: Basic;
Solubility: soluble in acidic water, methanol, acetone, ethyl acetate and benzene, difficulty soluble in basic water and insoluble in hexane;

and said antibiotic substance A 11725 IIa having the following properties:

Appearance: white crystals;
Molecular formula: $C_{37}H_{61}NO_{12}$;
Molecular weight: 711;
Melting point: 148° to 150° C.;
$[\alpha]_D$: +18.7° (C=1.0, methanol);
Ultra-violet absorption spectrum: as shown in FIG. 13;
Infra-red absorption spectrum: as shown in FIG. 14;
Nuclear magnetic resonance spectrum: as shown in FIG. 15;
Coloration reaction:
   Discoloration of aqueous potassium permanganate solution: +;
   Ninhydrin reaction, Sakaguchi's reaction and ferric chloride reaction: —;
Acidic or basic nature: Basic;
Solubility: soluble in acidic water, methanol, acetone, ethyl acetate and benzene, difficulty soluble in basic water and insoluble in hexane.

10. A process according to claim 9, wherein the chemical reagent is chromous chloride.

11. A pure culture of microorganism strain Micromonospora sp. A 11725 (NRRL 11452) which has been isolated from the soil and which is capable of producing at least one of the antibiotic substances A 11725 I, II and III upon being cultured in a nutrient medium.

* * * * *